United States Patent [19]
Yamazaki et al.

[11] Patent Number: 5,512,448
[45] Date of Patent: Apr. 30, 1996

[54] STABILIZATION OF PEROXIDASE CONJUGATES IN SOLUTION

[76] Inventors: Hiroshi Yamazaki, 22 Alderbrook Drive, Nepean, Ontario, Canada, K2H 5W5; Cameron S. Boyd, 31 Silver Horse Crescent, Kanata, Ontario, Canada, K2M 2J2

[21] Appl. No.: 234,925

[22] Filed: Apr. 28, 1994

[51] Int. Cl.$^6$ ............... G01N 33/53; C12N 9/08; C12N 9/96
[52] U.S. Cl. ............... 435/7.9; 435/28; 435/188; 435/962
[58] Field of Search ............... 435/7.9, 7.91–7.95, 435/28, 188, 967, 962; 436/528, 530, 828

[56] References Cited

U.S. PATENT DOCUMENTS

| | | | |
|---|---|---|---|
| 4,446,232 | 5/1984 | Liotta | 436/514 |
| 4,891,311 | 1/1990 | Anawis et al. | 435/7.9 |
| 4,931,385 | 6/1990 | Block et al. | 435/7.94 |
| 5,084,559 | 1/1992 | Profy | 436/828 |
| 5,155,024 | 10/1992 | Eikenberry | 435/7.9 |
| 5,169,757 | 12/1992 | Yamazaki et al. | 435/7.92 |

OTHER PUBLICATIONS

Aldrich Catalog 1988–1989 pp. 1245 and 1253.
Grant R. L. et al. Chemical Dictionary. McGraw–Hill, 1987, p. 461.
Vector Laboratories Incorporated. 1984 Catalog.
The Use of Synthetic Polymers for Preventing Enzyme Thermal Inactive—pp. 345 to 350—By Francesco Alfani, Istituto di Principi di Ingegneria Chimica, Universita di Napoli, P. le Tecchio, 80125 Napoli, Italy; and Maria Cantarella, Gabriella Cirielli, and Vicenzo Scardi, Istituto di Fisiologia Generale, Universita di Napoli, via Mezzocannone 8, 80134 Napoli, Italy.
Biotechnology Techniques, vol. 8, No. 2 (Feb. 1994) pp. 123 to 128, Use of Polyvinyl Alcohol as a Stabilizer of Peroxidase–Antibody Conjugate for Enzyme Immunoassay, by Scott Boyd and Hiroshi Yamazaki, Department of Biology and Institute of Biochemistry, Carleton University, Ottawa, Ontario, Canada, K1S 5B6.
Biotechnology Techniques, vol. 7, No. 9, (Sep. 1993) pp. 671 to 676, Stabilization of Peroxidase–Antibody Conjugate in Solution by Polyethylene Oxide, by Scott Boyd and Hiroshi Yamazaki, Department of Biology and Institute of Biochemistry, Carleton University, Ottawa, Ontario, Canada K1S 5B6.
H. F. Mark et al, eds., (1983). "Vinyl Polymers(Poly(Vinyl Alcohol)", in Encyclopedia of Chemical Technology, vol. 23, pp. 848 to 865, Toronto: John Wiley & Sons, Inc.
Academic Press, Inc., vol. 53, No. 4, 1973, Biochemical and Biophysical Research Communications, Immobilization of Enzymes Through Non–Covalent Binding to Substituted Agaroses, by B. H. J. Hofstee, with the technical assistance of N. Frank Otillio, Biochemistry Division, Palo Alto Medical Research Foundation, Palo Alto, California 94301.
Enzyme Microb. Technol., 1988, vol. 10, Aug., Influence of Additives on the Thermostability of Glucose Oxidase, by W. N. Ye, D. Combes and P. Monsan, Department of Genie Biochimique et Alimentaire, US–CNRS–No. 544, Institut National des Sciences Appliquees, avenue de Ragueil, 31077 Toulouse Cedex, France.

*Primary Examiner*—Mary E. Mosher
*Assistant Examiner*—Donna C. Wortman
*Attorney, Agent, or Firm*—Marcus & Associates

[57] ABSTRACT

A stabilized peroxidase conjugate is provided herein. Such conjugate includes a stabilizing quantity of polyethylene oxide or polyvinyl alcohol therein.

8 Claims, 3 Drawing Sheets

- PVA (9 - 10,000)(SA)
- PVA (124 - 186,000)(SA)
- PEO (100,000)(SA)
- PVA (9 - 10,000)(NSA)
- PVA (124 - 186,000)(NSA)
- PEO (100,000)(NSA)

- CONTROL
- 0.5% 9 - 10,000
- 1% 124 - 186,000

5,512,448

STABILIZATION OF PEROXIDASE CONJUGATES IN SOLUTION

BACKGROUND OF THE INVENTION

1. Field of the Invention

This invention relates to the stabilization of peroxidase conjugates in solution.

2. Description of the Prior Art

Enzyme immunoassay (EIA) provides simple and rapid detection of a variety of antigens, e.g., pathogens, toxins, and environmental pollutants in addition to antibodies for serodiagnosis. In EIA, enzyme conjugates of immunoreactants (antibodies or antigens) are used to quantitate sample immunoreactants by measuring the amounts of enzyme products. Since the enzyme conjugates have limited stability at ambient temperatures, refrigeration is normally required for their transportation and storage. Horseradish peroxidase (HRP) is a popular EIA enzyme because of its low price and high specific activity. HRP is a glycoprotein of relatively high carbohydrate content (e.g., 20%).

HRP is also used in other conjugates. These include HRP-labeled lectins which are useful for the characterization of glycoproteins or carbohydrates-containing substances because of lectins' specific interaction with carbohydrate moieties. HRP-protein A and G are other HRP conjugates which are extensively used in the detection of antibodies because of specific interaction between these proteins and antibodies. HRP-streptavidin or avidin is used to detect any biotin-containing substances because of specific interaction between streptavidin or avidin and biotin.

Since field EIA would facilitate control of pathogens, diseases, and pollutants, it is important to develop methods for stabilizing the activity of enzyme-conjugates at ambient temperatures. For field EIA applications, it is desirable to have a conjugate suspension that can be used without further dilution prior to EIA.

SUMMARY OF THE INVENTION

Aims of the Invention

It is therefore an object of this invention to provide enzyme-conjugates whose activity is stabilized at ambient temperature.

It is another object of this invention to provide a stabilizer which does not interfere with immunoreaction at stabilizing concentrations.

It is believed, and it is a basis of the present invention that, binding of a high molecular weight polymer onto the carbohydrate moiety of HRP would stabilize HRP by restricting conformational changes leading to inactivation.

Thus, the present invention resides in the discovery that the addition of polyethylene oxide (PEO) to HRP conjugate solutions greatly stabilizes its enzyme activity, allowing storage at ambient temperatures. The present invention resides in the discovery that polyethylene oxide (PEO) effectively stabilizes the peroxidase activity of a peroxidase-antibody conjugate, and that PEO had no adverse effects on immunoassays when the conjugate suspension was diluted 100 times prior to EIA.

The present invention also resides in the discovery that polyvinyl alcohol (PVA) of a particular MW and degree of hydrolysis not only stabilizes peroxidase-antibody conjugate, but also does not affect immunoreaction at stabilizing concentrations. Stabilization of the conjugate at ambient temperatures which will not only economize EIA but will also expand its application under field conditions which lack refrigeration.

STATEMENTS OF INVENTION

The present invention provides a peroxidase conjugate including a stabilizing quantity of polyethylene oxide or polyvinyl alcohol therein.

FEATURES OF THE INVENTION

In one feature of the invention, a peroxidase-antibody conjugate is provided.

In another feature of the invention, a peroxidas-lectin conjugate is provided.

In yet another feature of the invention, a peroxidase-protein A conjugate is provided.

In still another feature of the invention, a peroxidase-protein G conjugate is provided.

In a still further feature of the invention, a peroxidase-streptavidin conjugate is provided.

In still a further feature of the invention, a peroxidase-avidin conjugate is provided.

In one feature of the invention the conjugate includes up to about 2% weight per volume (w/v) of polyethylene oxide having a molecular weight of about 100,000–600,000.

One variation of such feature involves the use of about 2% to about 10% weight per volume (w/v) for polyethylene oxide of molecular weight about 100,000.

Another variation of such feature involves the use of about 2% to about 5% weight per volume (w/v) for polyethylene oxide of molecular weight about 300,000.

Yet another variation of such feature involves the use of about 2% weight per volume (w/v) for polyethylene oxide of molecular weight about 600,000.

Still another variation of such feature involves the use of about 2% weight per volume (w/v) for polyethylene oxide of molecular weight about 900,000.

A further variation of such feature involves the use of about 1% weight per volume (w/v) for polyethylene oxide of molecular weight about 5,000,000.

In another feature of the invention the conjugate includes from about 0.5 to about 10% weight per volume (w/v) of polyvinyl alcohol of molecular weight up to about 10,000.

In another feature of the invention the conjugate includes from about 1 to about 5% weight per volume (w/v) of polyvinyl alcohol of molecular weight about 124,000–186,000.

In another feature of the invention the stabilized peroxidase-antibody conjugate is adsorbed on a cloth substrate, e.g., a polyester cloth substrate.

BRIEF DESCRIPTION OF THE DRAWINGS

In the accompanying drawings.

DESCRIPTION OF PREFERRED EMBODIMENTS

Figure 1:
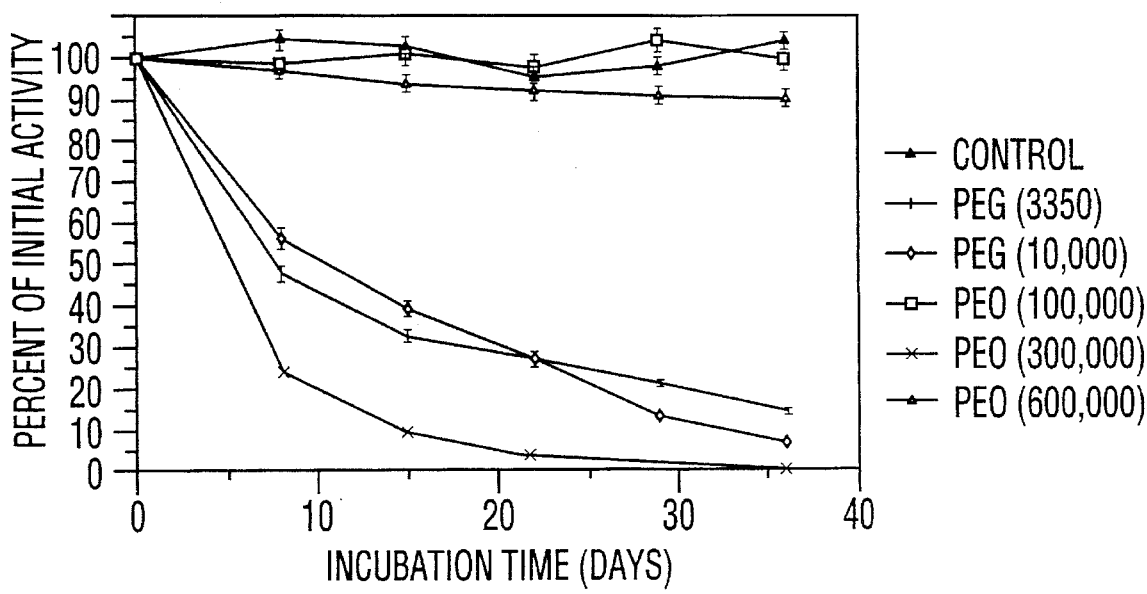
FIG. 1 is a graph showing the effects of various additives on the HRP activity of the HRP conjugate.

The following are examples of the invention. However, before describing such examples, the following is a disclosure of the materials used.

The following materials were obtained from Sigma Chemical Co.: Goat anti-rabbit IgG antibody peroxidase conjugate (HRP conjugate) (A-6154), rabbit IgG (I-5006), bovine alkaline phosphatase (AP) (P-0405), horseradish peroxidase (HRP) (P-6782), p-nitrophenol phosphate (Sigma No. 104), 3,3'5,5'-tetramethylbenzidine (TMB) (T-2885), EDTA tetrasodium salt (ED4SS), citric acid monohydrate (C-1909), polyethylene glycol (PEG) 3350 (P-3640) and PEG 10,000 (P-6667), PVA (MW, 30,000–70,000) (P-8136), PVA (MW 70,000–100,000) and thimerosal (T-5125). Aldrich Chemical Co. supplied sodium perborate ($NaBO_4$) tetrahydrate (24,412-0), polyethylene oxide (PEO) MW, 100,000 (18,198-6), PEO MW, 300,000 (18,200-1) PEO MW, 600,000 (18,202-8), PEO, MW, 900,000 (18,945-6) and PEO MW, 5,000,000 (18,957-2). PVA (MW, 9,000–10,000, 80% hydrolyzed) (36,062-7), PVA (MW, 13,000–23,000, 98% hydrolyzed) (34,840-6), and PVA (MW, 124,000–186,000, 99+ % hydrolyzed) (36,306-5). The Blocker (non-fat milk) (170-6404) was obtained from Bio Rad.

EXAMPLE 1

Determining the Effects of PEG and PEO on HRP Activity of the Conjugate

HRP conjugate was suspended in PBS (0.01M sodium phosphate pH 7.3 buffer in 0.85% NaCl) containing 0.01% thimerosal (PBSTh) and 0 to 10% of PEG or PEO of differing molecular weights. The concentration of the HRP conjugate in the suspension was adjusted to that the initial HRP activity, when diluted 100 times for assay, produced a suitable density ($A_{370}$ of 1 to 2) of TMB colour product during a 10 min. reaction. The suspensions were incubated at 30° C. and periodically assayed for HRP activity following a 100 times dilution with PBS containing 0.05% Tween 20 (PBST).

EXAMPLE 2

Determining the Effects of PEO on the Enzyme Activity of Free HRP and AP

HRP was suspended in PBS containing 0.01% benzalkonium chloride (PBSB) and 2% PEO (MW 100,000), followed by a 15 day incubation at 30° C. As an antimicrobial agent, benzalkonium chloride was used instead of thimerosal which showed toxicity to free HRP. The concentration of HRP was adjusted so that its initial HRP activity, when diluted 100 times, produced a sufficient density ($A_{370}$ of 1 to 2) during a 5 min. reaction of TMB colour product.

Alkaline phosphatase (AP) was incubated at 37° C. for 15 days in PBS containing 0.1% sodium azide (PBSNa) (added as an antimicrobial agent) and 2% PEO (MW 100,000). The concentration of AP was adjusted so that its initial activity, when diluted 100 times, yielded a sufficient density ($A_{405}$ of 1 or 2) of the colour product during a 5 min. reaction.

EXAMPLE 3

Horseradish Peroxidase Assay

One-tenth ml of a liquid sample or a cloth segment (6 mm square) containing the HRP conjugate was incubated with 1 ml of a TMB indicator system at room temperature. The absorbency of the resulting colour at 370 nm ($A_{370}$) was measured after the reaction was stopped with 0.2M NaF (0.1 ml). The TMB indicator system was prepared by mixing 2.5 ml of TMB (2 mg/ml ethanol) with a solution consisting of 0.21 g citric acid $H_2O$, 0.42 g EDTA 4 Na, 0.03 g $NaBO_4 4H_2O$ and 100 ml $H_2O$.

EXAMPLE 4

Alkaline Phosphatase Assay

A liquid sample containing AP was diluted 100 times with 1M diethanolamine buffer (pH 9.8) containing $5 \times 10^4$M $MgCl_2$ and incubated at 37° C. with 10 volumes of 15 mM p-nitrophenol phosphate in the same buffer. After 5 min., the reaction was stopped by adding an equal volume of 0.1 M EDTA (pH 9.8) and the absorbency at 405 nm ($A_{405}$) was measured.

EXAMPLE 5

Effect of PEO on the Immunoreactivity of HRP Conjugate

Cloth-based EIA was used to assay the immunoreactivity of the HRP conjugate. Segments (6 mm square) of polyester cloth (DuPont, Sontara 8100) were washed with ethanol for a few minutes, followed by PBS and then blotted. Each segment was incubated with 50 μl of rabbit IgG (100 μg/ml PBS). After 16 h at 30° C., the segments were washed with PBST and blotted. The HRP conjugate was suspended in PBSTh containing 2% PEO (MW 100,000) or PBSTh alone (control). The suspensions were incubated at 30° C., with samples being periodically removed and tested, following a 100-fold dilution in PBS. Each rabbit IgG coated cloth was incubated with 50 μl of the diluted conjugate for 30 min. at room temperature. The cloth was washed 5 times with PBST, blotted and assayed for HRP as previously described.

EXAMPLE 6

Effect of PVA on Peroxidase Activity of the HRP Conjugate

HRP conjugate was suspended in PBS (0.01M sodium phosphate pH 7.3 buffer in 0.85% NaCl) containing 0.01% thimerosal (PBSTh) and 0 to 10% (w/v) of PVA of various molecular weights. The concentration of the HRP conjugate in the different PVA solutions was adjusted so that the initial HRP activity, following a 100 times dilution in PBS, produced a suitable density ($A_{370}$ of 1 to 2) of TMB colour product during a 10 min. reaction. The HRP conjugate suspensions were incubated for 36 days at 30° C. and then assayed for peroxidase activity.

EXAMPLE 7

Effect of PVA and PEO on Immunoreaction

The immunoreaction between rabbit IgG and anti-rabbit IgG was assayed using cloth-based EIA. Segments (6 mm square) of polyester cloth (DuPont, Sontara 8100) were soaked in ethanol for a few min. washed 5×PBS, and blotted. Each cloth segment was incubated with rabbit IgG (5 µg in PBS/cloth) for 16 h at 30° C. to coat the cloth with rabbit IgG. The rabbit IgG-cloths were washed with 5×PBST (PBS containing 0.05% Tween 20) and then incubated in 0.5% Blocker (w/v) in PBS for 1 h. HRP conjugate was suspended in various solutions of PVA or PEO in PBS for 30 min. The concentration of the HRP conjugate suspensions was adjusted so that peroxidase activity could be assayed without further dilution steps. Following washing with 3 ×PBS and blotting, the rabbit IgG-cloths were reacted to the different HRP conjugate suspensions (30 µl/cloth for 10 min. at room temperature. The cloths were washed with 5× PBST, blotted, and assayed for peroxidase activity.

EXAMPLE 8

Effect of PVA on Conjugate Activity

HRP conjugate was added to solutions of PBSTh containing 0.5% PVA (MW 9,000–10,000) or 1% PVA (MW 124,000–186,000) and then incubated at 30° C. for 36 days. Samples were removed from each HRP conjugate suspension at regular time intervals and reacted to rabbit IgG-cloths prepared as above (30 µl of sample/cloth). The cloths were washed with 5×PBST, blotted, and assayed for peroxidase activity.

EXAMPLE 9

Horseradish Peroxidase Assay

Fifty µl of a HRP conjugate suspension sample or a rabbit IgG-cloth segment reacted to HRP conjugate was incubated in 1 ml of a TMB indicator system. Following a 10 min. incubation on a New Brunswick Gyrotary Shaker (setting 5) at room temperature, the reaction was stopped with 0.2M NaF (0.1 ml/cloth). The absorbency of the resulting colour at 370 nm ($A_{370}$) was measured. The TMB indicator system was prepared by mixing 2.5 ml of TMB (2 mg/ml ethanol) with a solution consisting of 0.21 g citric acid $H_2O$, 0.42 g EDTA 4 Na, 0.03 g $NaBO_4 4H_2O$, and 100 ml $H_2O$.

Operation of Preferred Embodiments

From the above examples, it is seen that goat anti-rabbit IgG antibody HRP conjugate was used as a model to examine the stabilization effect of PEG and PEO on the HRP conjugate. These water-soluble polymers (PEG and PEO) were added to the conjugate solutions and incubated at 30° C. for 36 days in the presence of thimerosal (added as an anti-microbial agent). FIG. 1 shows the effects of various additives on the HRP activity of the HRP conjugate. The HRP conjugate suspension was stored in PBSTh (control) or 2% additive in PBSTh for a period of 36 days at 30° C. The activity of the HRP conjugate was measured as described in Methods. Average absorbency is plotted as percent of initial activity. The vertical bars represent standard deviation (n= 6). FIG. 1 shows that HRP activity in the conjugate remained essentially unchanged in the presence of 2% PEO, whereas the activity declined in the absence of PEO. The nearly complete stabilization effect occurred independent of the molecular weights of PEO used between 100,000 and 600,000. PEO of MW up to 5,000,000 exhibited similar stabilization effects at 1 to 2% weight per volume (w/v). While PEG of MW 10,000 showed only partial stabilization during 15 days of incubation, PEG of MW 3350 destabilized the HRP activity.

Figure 2:
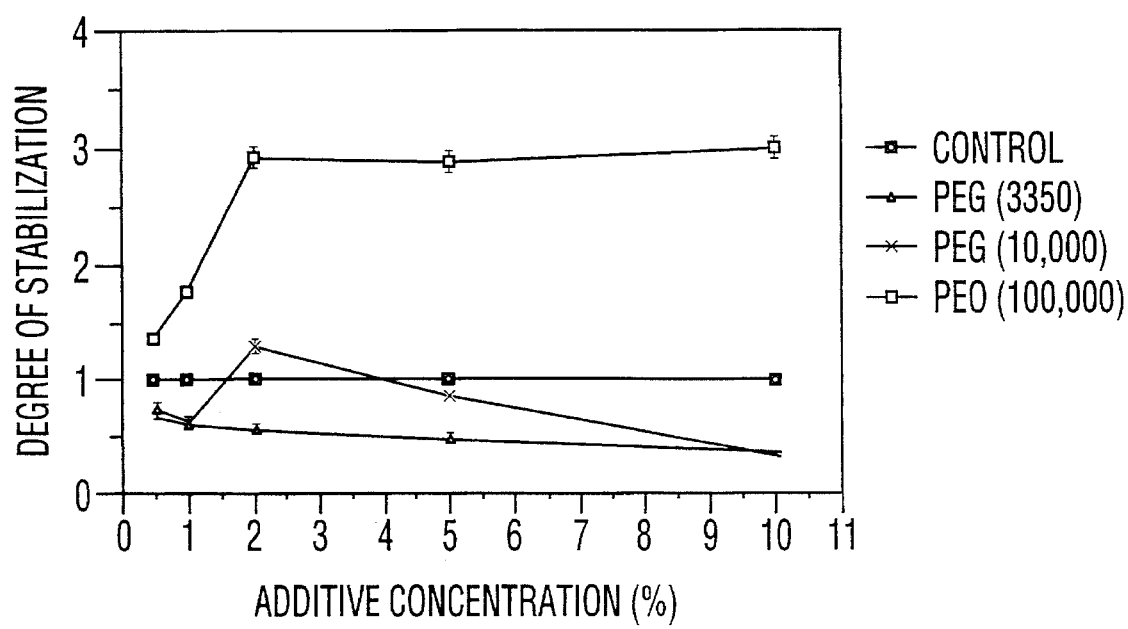
FIG. 2 is a graph showing the effect of varying the concentrations of additives on their ability to stabilize enzyme activity.

FIG. 2 shows the effect of varying the concentrations of additives on their ability to stabilize enzyme activity the plotted values represent the degrees of stabilization (the ratio of HRP activity with additives to control without additives) on day 15. The vertical bars represent standard deviations (n= 6).

FIG. 2 shows the effect that varying concentrations of PEG and PEO had on the degree of stabilization (HRP activity with additives/HRP activity without additives) measured after a 15 day incubation at 30° C. For PEO (MW 100,000), stabilization reached a maximum plateau at 2%. Destabilization occurred at concentration beyond 2% for PEG (MW 10,000 and MW 3350).

While it is not desired to be bound by theory, it is believed that PEG and PEO, which are water-soluble polymers, are capable of forming hydrogen bonds through their ether oxygen atoms. Thus, PEG and PEO polymers of high molecular weight can interact with hydrogen atoms on the exterior carbohydrate moiety of HRP.

PVA may be produced through polymerization of vinyl acetate and subsequent hydrolysis. Thus, PVA is available in various MW and degrees of hydrolysis. While it is not desired to be bound by theory, it is believed that PVA is known to stabilize acid phosphatase.

Figure 3:
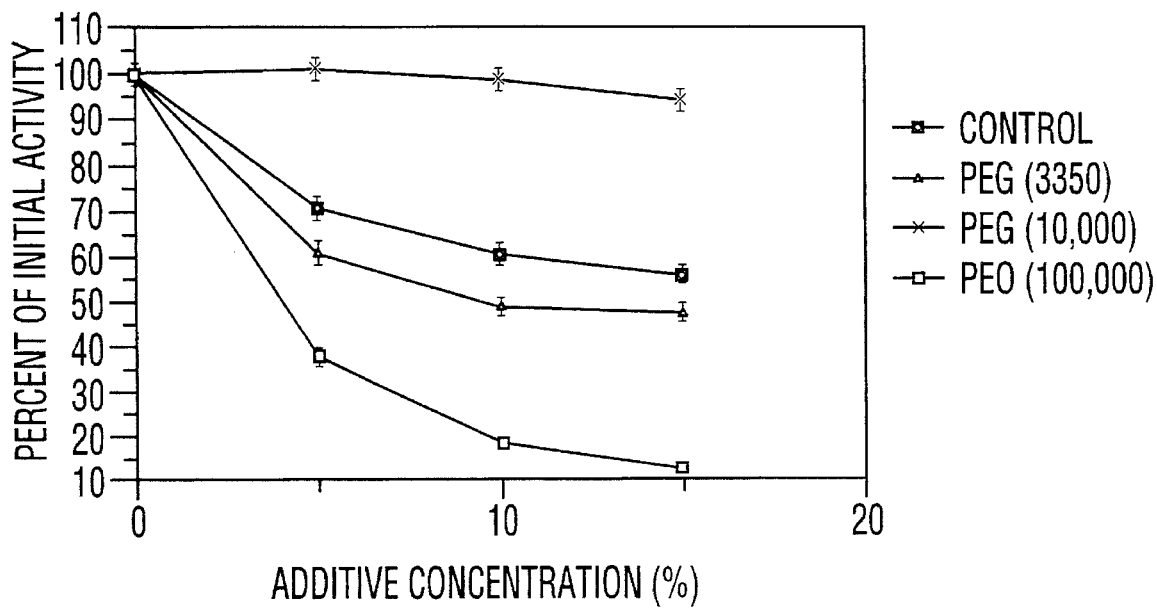
FIG. 3 is a graph showing the effect of PEO on the enzyme activity of free HRP or alkaline phosphatase (AP)

While it is not desired to be bound by theory, it is believed that PEO stabilized the HRP conjugate by directly interacting with HRP. The effect of PEO on free HRP and bovine AP was investigated. AP, another popular EIA enzyme, has a hydrophobic exterior which strongly interacts with hydrophobic supports. FIG. 3 shows the effect of PEO on the enzyme activity of free HRP or AP. HRP or AP was stored in PBSB (or PBSNa for AP) (control) or PBSB (or PBSNa)+ 2% PEO (MW) 100,000 for a period of 15 days at 30° C. (for HRP) or 37° C. (for AP). Average absorbency is plotted as percent of initial activity. The vertical bars represent standard deviations (n= 6). FIG. 3 shows that 2% PEO (MW 100,000) stabilized free HRP but destabilized free AP. While it is not desired to be bound by theory, it is likely that stabilization of HRP conjugate may be ascribed to the direct action of PEO on HRP.

Figure 4:
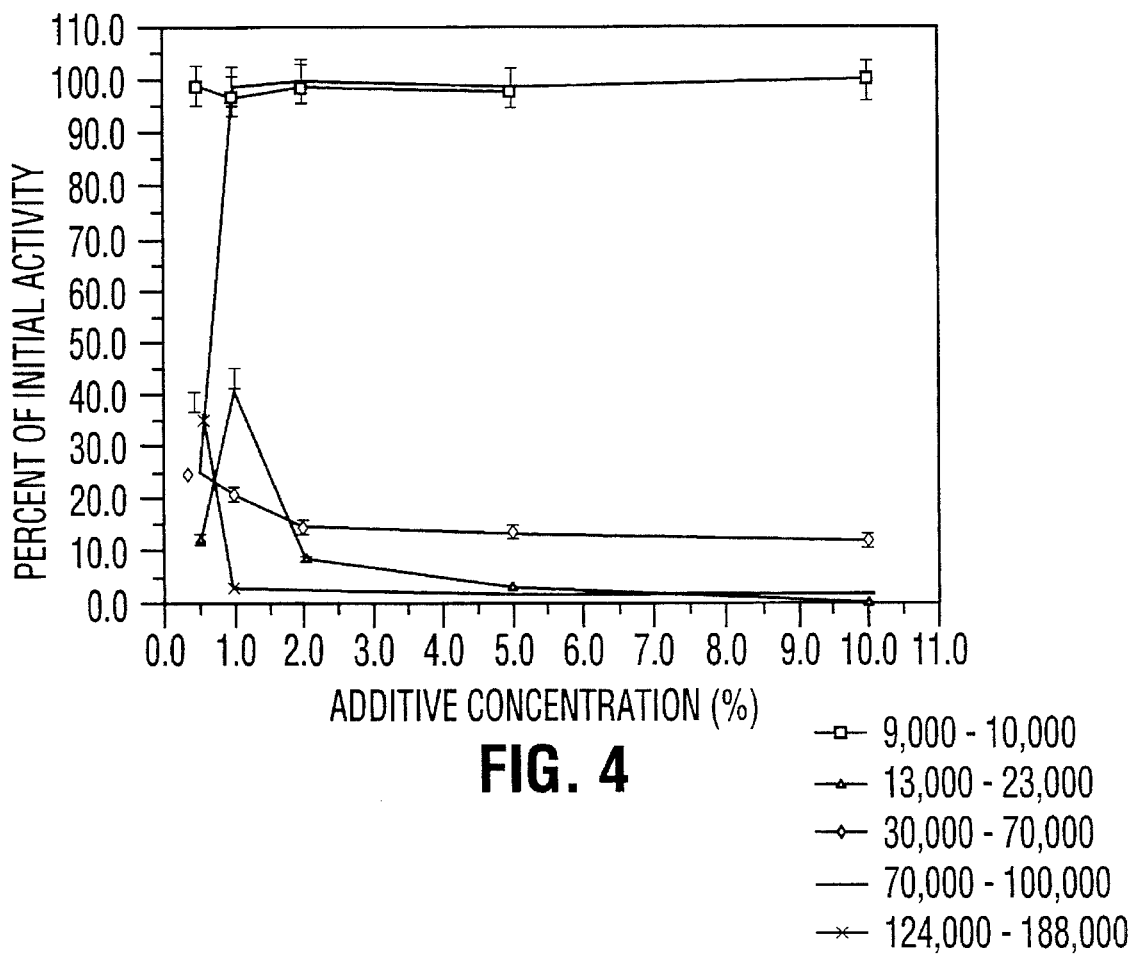
FIG. 4 is a graph showing the effects of various concentrations of the different PVA species on the peroxidase activity of the HRP conjugate.

To examine the stabilizing capacity of PVA, goat anti-rabbit IgG antibody peroxidase conjugate (HRP conjugate) was suspended in a series of solutions of PVA of various molecular activity was then assayed following a 36 day incubation at 30° C., as described above, stabilization of the HRP conjugate by PEO. FIG. 4 shows the effects of various concentrations of the different PVA species on the peroxidase activity of the HRP conjugate. The HRP conjugate was stored in PBSTh (control) or PVA in PBSTh for a period of 36 days at 30° C. The peroxidase activity of the HRP conjugate was measured as described in Methods. Average absorbency was plotted as percent of initial activity at time 0. The peroxidase activity of the conjugate without additives was 13.6% of the initial activity. The vertical bars represent standard deviations (n= 6). FIG. 4 shows that 0.5 to 10% PVA (MW 9,000–10,000) and 1 to 5% PVA (MW 124,000–186,000) provided the greatest peroxidase stabilization effect: HRP conjugate showed no significant decrease in peroxidase activity as previously observed with 2% PEO (MW 100,000).

While the other PVA species showed a stabilizing effect as compared to the untreated control at certain concentrations, stabilization was not complete. Higher concentrations of PVA (MW13,000–23,000 and 70,000–100,000) actually had a denaturing effect upon the peroxidase activity of the HRP conjugate.

Figure 5:
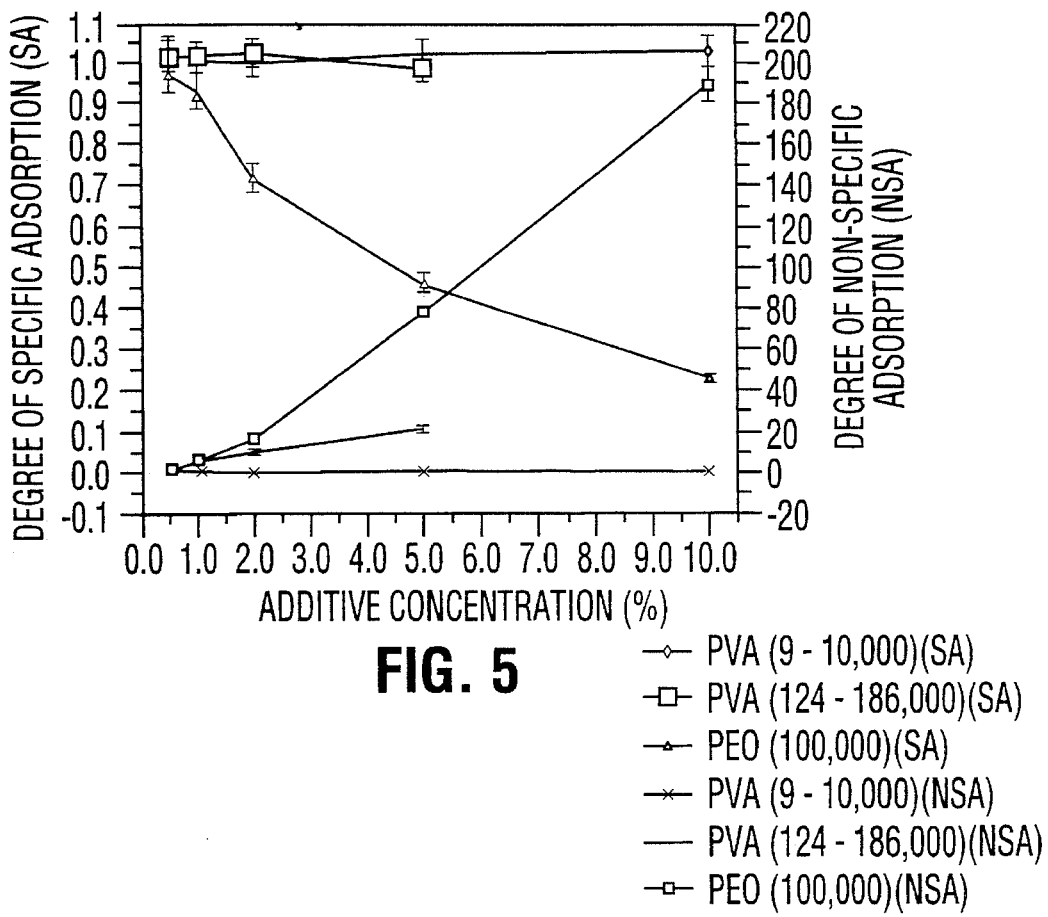
FIG. 5 is a graph showing the effect of various concentrations of additives on immunoreaction.

Since PVA (MW9,000–10,000 and 124,000–186,000) showed complete stabilization of the HRP conjugate, their effect on immunoreaction was compared to PEO (MW 100,000) at various concentrations. HRP conjugate was incubated in the additive solutions in PBS for 1 h and then reacted to rabbit IgG-cloth. FIG. 5 shows the effect of various concentrations of additives on immunoreaction. HRP conjugate was reacted to cloth with or without rabbit IgG (a model antigen) in the presence of stabilizing concentrations of PVA or PEO. The peroxidase activity of the adsorbed HRP conjugate was measured as described in Methods, and used to determine the effect of PVA or PEO on specific and non-specific HRP conjugate adsorption. The results were plotted as the ratio specific adsorption of the HRP conjugate with additive to specific adsorption without additive, and non-specific adsorption with additive to non-specific adsorption without additive. The vertical bars represent standard deviations (n= 6). FIG. 5 shows that in cloth-based EIA, the presence of 0.5 to 10% PVA (MW 9,000–10,000) or 0.5 to 5% PVA (MW 124,000–186,000) in the HRP conjugate suspension did not affect the specific adsorption of the HRP conjugate. With PEO, however, the amount of specifically adsorbed HRP conjugate decreased rapidly with increasing PEO concentration. For maximum stabilizing effect, the concentration of PEO (MW 100,000) must be $\geq$ 2%. FIG. 5 shows that the ratio of specific adsorption of the HRP conjugate with PEO to specific adsorption of the HRP conjugate without PEO is approximately 0.71 when the PEO concentration is 2% and 0.24 when the PEO concentration is 10%. Thus, the presence of stabilizing concentrations of PEO (MW 100,000) caused substantial inhibition of the immunoreaction between the antibody conjugate and the antigen immobilized on the cloth.

FIG. 5 also shows the effect of additives on the non-specific adsorption (background) of the HRP conjugate. The presence of 2% PEO (MW 100,000) in the HRP conjugate produced 16× greater background than that of the HRP conjugate without PEO. Higher concentrations of PEO caused even greater background. The presence of 0.5 to 10% PVA (MW 9,000–10,000) or 0.5 to 1% PVA (MW 124,000–186,000) resulted in no significant increase in background. However, with PVA (MW 124,000–186,000), the background increased when the PVA concentration in the HRP conjugate suspension was greater than 1%. If the HRP conjugate stabilized by PVA is to be used for EIA without prior dilution, the lowest possible concentration of PVA should be utilized in order to provide the lowest viscosity. In EIA systems where the antigens and antibodies are not in close proximity, increasing viscosity results in decreasing rates of immunoreaction. Thus, 0.5% PVA (MW 9,000–10,000) or 1% PVA (MW 124,000–186,000) should be used to obtain optimal stabilizing effect while minimizing viscosity and background.

Figure 6:
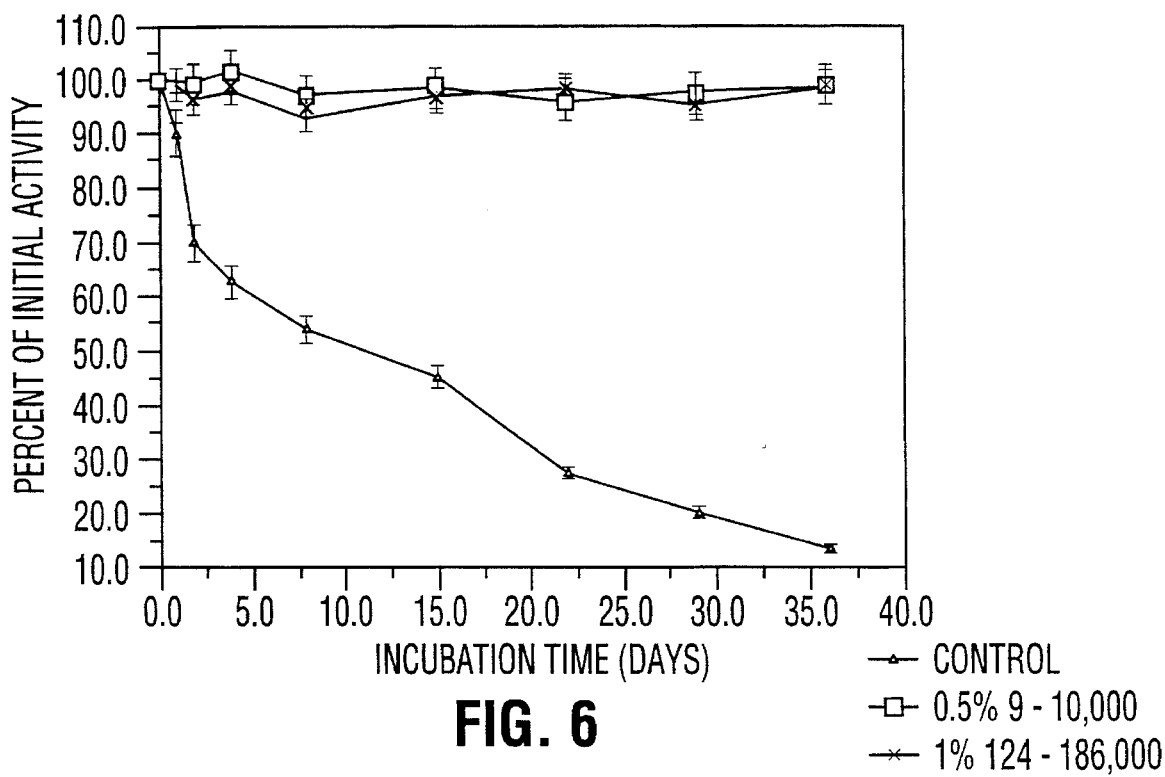
FIG. 6 is a graph showing the effect bf different PVA solutions on the conjugate activity.

It has been shown that PVA (MW 9,000–10,000 and 124,000–186,000) can stabilize the peroxidase activity of the HRP conjugate. The effect of PVA on the conjugate activity used in EIA was also studied. HRP conjugate was incubated in PBSTh containing either 0.5% PVA (MW 9,000–10,000) or 1% PVA (MW 124,000–186,000) for 36 days at 30° C. At regular time intervals, samples of the HRP conjugate suspensions were removed, reacted to rabbit-IgG-cloths, and assayed for peroxidase activity. FIG. 6 shows the effect of different PVA solutions on the conjugate activity. HRP conjugate was incubated in PBSTh (control) or PVA in PBSTh for 36 days at 30° C. At regular time intervals, samples of the HRP conjugate suspension were reacted to rabbit IgG-cloths and then assayed for peroxidase activity as described in Methods. Average absorbency was plotted as percent of initial activity at time 0. The vertical bars represent standard deviations (n= 6). FIG. 6 shows that HRP conjugate activity is stable throughout the 36 day test period when stored in 0.5% PVA (MW 9,000–10,000) or 1% PVA (MW 124,000–186,000). HRP conjugate stored in the absence of PVA demonstrated a continual decrease in HRP conjugate activity over time due to loss of peroxidase activity rather than antibody activity.

PEO can be added to stabilize HRP conjugate in a stock solution for EIA. Prior to EIA, the conjugate will be diluted at least 100 times with PBS containing 0.05% Tween 20 (PBST). The presence of small amounts of PEO (<0.02%) should not interfere with immunoreaction in EIA. To test this possibility, cloth-based EIA was employed. Rabbit-IgG (an antigen) was immobilized onto polyester cloth. The anti-rabbit IgG HRP conjugate was suspended in PBS (control) or PBS containing 2% PEO (MW 100,000), and then diluted 100 times with PBST. The antigen coated cloths were allowed to react with the diluted conjugate suspensions. No significant difference in the EIA signals was observed whether the conjugate was suspended in PEO or not. During storage at 30° C. for 36 days, the conjugate lost little immunoreactivity (as well as HRP activity).

It has been previously proposed that the stabilization effect observed for certain enzymes in the presence of additives is a result of decreased water activity in the presence of the enzyme's solvent medium. For both PVA and PEO stabilization, the concentration of the additive present in the HRP conjugate suspension is very low. While it is not desired to be bound by any theory, it is believed that PVA or PEO conjugate stabilization results from the direct interaction between the additive and conjugate.

The following are known features of PVA: (i) as the molecular weight of PVA increases, the adhesion of the polymer to hydrophilic surfaces increases and (ii) as the degree of hydrolysis in the PVA molecules decreases, the adhesion to hydrophobic surfaces increases. While it is not desired to be bound by theory, it is believed that the high molecular weight and high degree of hydrolysis (99+ %) of PVA (MW 124,000–186,000) allows it to interact very strongly with hydrophilic sites on the HRP conjugate through H-bond formation between alcohol groups in the PVA and H-atoms in the carbohydrate moiety of HRP. Similarly, the low molecular weight and low degree of hydrolysis (80%) of PVA (MW 9,000–10,000) permits hydrophobic interactions between the hydrocarbon backbone of PVA (MW 9,000–10,000) permits hydrophobic interactions between the hydrocarbon backbone of PVA and hydrophobic patches on the surface of HRP. Like PVA, while it is not desired to be bound by theory, it is believed that PEO (MW 100,00) stabilizes the HRP conjugate through H-bond information between the ether oxygen atoms in PEO and H-atoms in the carbohydrate moiety of HRP, and hydrophobic interactions between multiple ethylene residues of PEO and hydrophobic patches on HRP. These interactions stabilize the HRP conjugate by restricting its freedom to take inactive conformations. The resulting complex remains soluble because of the ampiphilic nature of the interacting polymer.

Thus, by the present invention, it has been found that the inclusion of polyethylene oxide to a peroxidase-antibody conjugate suspension greatly stabilized conjugate activity which showed no loss during storage for 36 days at 30° C. This stabilization not only economizes enzyme immunoassays but also permits its use under field conditions lacking refrigeration. It has also been found that the activity of a peroxidase-antibody conjugate was greatly stabilized while in solution through the addition of polyvinyl alcohol (PVA). This stabilizing effect was dependent upon the molecular weight and degree of hydrolysis of the PVA used. The concentrations of PVA necessary for maximum stabilization had no adverse effects upon enzyme immunoassay. Thus, the conjugate stabilized by PVA can be used without dilution for enzyme immunoassay, and without need of refrigeration during transport and storage.

In summary, the inclusion of PEO in a HRP conjugate stock solution markedly stabilizes the HRP activity in the conjugate. The stabilization eliminates the need for refrigeration of the conjugate during transport and field EIA. Furthermore, the addition of PVA to a HRP conjugate suspension markedly stabilizes the peroxidase activity of the conjugate. The immunoactivity of the HRP conjugate is not inhibited by the presence of a stabilizing concentration of PVA. The use of PVA as a stabilizer, therefore, not only permits the use of HRP conjugate without dilution prior to EIA, but also eliminates the need for refrigeration of the conjugate during transportation and field EIA.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A peroxidase conjugate composition consisting essentially of (i) said peroxidase which is conjugated to a member selected from the group consisting of an antibody, a lectin, protein A, protein G, streptavindin, and avidin, and (ii) a polymer selected from the group consisting of: up to about 2 % weight per volume (w/v) of polyethylene oxide having a molecular weight of about 100,000 to about 600,000; about 2% to about 10% weight per volume (w/v) of polyethylene oxide having a molecular weight of about 100,000; from about 2% to about 5% weight per volume (w/v) of polyethylene oxide having a molecular weight of about 300,000; about 2% weight per volume (w/v) of polyethylene oxide having a molecular weight of about 600,000; about 2% weight per volume (w/v) of polyethylene oxide having a molecular weight of about 900,000; about 1% weight per volume of polyethylene oxide having a molecular weight of about 5,000,000; from about 0.5 to about 10% weight per volume (w/v) of polyvinyl alcohol of molecular weight of up to about 10,000; and from about 1 to about 5% weight per volume (w/v) of polyvinyl alcohol of molecular weight of about 124,000 to 186,000; wherein said amounts of said selected polymers are sufficient to stabilize the enzymatic activity of said peroxidase in said peroxidase conjugate.

2. The peroxidase conjugate composition of claim 1, wherein said conjugate is a peroxidase-lectin conjugate.

3. The peroxidase conjugate composition of claim 1, wherein said conjugate is a peroxidase-protein A conjugate.

4. The peroxidase conjugate composition of claim 1, wherein said conjugate is a peroxidase-protein G conjugate.

5. The peroxidase conjugate composition of claim 1, wherein said conjugate is a peroxidase-streptavidin conjugate.

6. The peroxidase conjugate composition of claim 1, wherein said conjugate is a peroxidase-avidin conjugate.

7. A combination comprising the peroxidase-antibody conjugate composition of claim 1 which is adsorbed on a cloth substrate.

8. The combination of claim 7 wherein said cloth substrate is a polyester cloth substrate.

* * * * *